United States Patent [19]

Huynh Dinh et al.

[11] Patent Number: 4,845,205
[45] Date of Patent: Jul. 4, 1989

[54] 2,N6-DISUBSTITUTED AND 2,N6-TRISUBSTITUTED ADENOSINE-3'-PHOSPHORAMIDITES

[75] Inventors: Tam Huynh Dinh, Croissy/Seine; Catherine Gouyette, Vanves; Jean Igolen, Le Mesnil St. Denis, all of France

[73] Assignees: Institut Pasteur; Centre National de la Recherce Scientifique, both of Paris, France

[21] Appl. No.: 822,639

[22] Filed: Jan. 8, 1986

[30] Foreign Application Priority Data

Jan. 8, 1985 [FR] France ............................. 85 00203

[51] Int. Cl.$^4$ ...................... C07H 19/06; C07H 19/10
[52] U.S. Cl. ........................................ 536/28; 536/27; 536/29
[58] Field of Search ...................... 536/27, 28

[56] References Cited

U.S. PATENT DOCUMENTS

| | | | |
|---|---|---|---|
| 3,114,751 | 12/1963 | Whetstone | 536/26 |
| 3,308,036 | 3/1967 | Nakayama et al. | 536/27 |
| 3,838,147 | 9/1974 | Pohlke et al. | 536/26 |
| 3,845,035 | 10/1974 | Kampe et al. | 536/26 |
| 3,910,883 | 10/1975 | Kikugawa et al. | 536/26 |
| 3,936,439 | 2/1976 | Marumoto et al. | 536/26 |
| 4,415,732 | 11/1983 | Caruthers et al. | 536/27 |
| 4,500,707 | 2/1985 | Caruthers et al. | 536/27 |

OTHER PUBLICATIONS

W. L. Sung, "Chemical Conversion of Thymidine into 5-Methyl-2'-deoxycytidine", J.C.S. Chem, Comm., (1981), p. 1089.

J. Davoll, "A Synthesis of Crotonoside", J.A.C.S., vol. 73, (1951), pp. 3174-3176.

K. Itakura et al., "Solid-Phase Synthesis of Polynucleotides", Nucleic Acids Research, (1980), pp. 5473-5489.

Gergen et al., Nucleic Acids Research, vol. 7, (1979), pp. 2115-2137.

Beiter et al., Tetrahedron Letters, vol. 25, No. 19, (1984), pp. 1975-1978.

Chemical Abstracts, vol. 80, (1974), No. 96289.

L. D. Townsend et al., ed. Nucleic Acid Chemistry, (1978), p. 565.

Primary Examiner—Ronald W. Griffin
Assistant Examiner—L. Eric Crane
Attorney, Agent, or Firm—Fleit, Jacobson, Cohn, Price, Holman & Stern

[57] ABSTRACT

The invention concerns 2,N6-disubstituted and 2,N6-trisubstituted adenosine nucleosides in which the sugar component is substituted at position 3' or position 5' by a phosphite or phosphoramidite group of the formula:

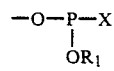

$R_1$ representing a lower alkyl or $-(CH_2)_n-CN$ with n being an integer between 1 and 4, and X representing a halogen or an amine group. These nucleosides make it possible to prepare sequences of nucleotides usable, in particular, as probes in the field of analyses and biological extractions.

6 Claims, No Drawings

2,N⁶-DISUBSTITUTED AND 2,N⁶-TRISUBSTITUTED ADENOSINE-3'-PHOSPHORAMIDITES

The object of the invention are novel nucleosides of adenosine, their preparation and biological applications, more especially, the synthesis of nucleotide sequences which can be used, in particular, as probes in biological analyses and extractions.

In the application FR No. 84 13095 of Aug. 22, 1984 made in the name of the applicants, probes were described consisting of oligonucleotide fragments bearing, as purine bases, modified adenine moieties, namely adenine moieties capable of forming three hydrogen bonds with the reactive groups of the pyrimidine bases (thymine, uracil).

The adenine moieties in question are modified preferably by the introduction at the carbon atom at position 2 of the pyrimidine ring of a group such as $-NH_2$, $-OH$ or $-SH$, the group $-NH_2$ being particularly preferred.

According to a preferred embodiment of the above probes, at least some of the adenine moieties of the oligonucleotide fragments are represented by the formula (a):

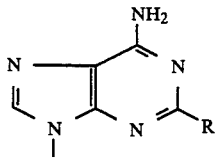

in which R represents a group $-NH_2$, $-OH$ or $-SH$.

The oligonucleotide fragments constituting the probes are prepared according to classical methods, preferably on a solid phase, by coupling a group in position 3' of the sugar component of a given nucleotide with a group in position 5' of the sugar component of another nucleotide, the latter being attached, if appropriate, to a polymeric support.

The expression "sugar component" refers, in the description and the claims, to both a ribose component and a desoxyribose component.

For these syntheses it is obviously important to have on hand nucleosides which are readily prepared and of high reactivity.

Developments in this area in the laboratory of the inventors have led them to the finding that by introducing defined phosphorus derivatives into the sugar component of the adenine modified as above, it is possible to prepare a family of nucleosides endowed with favourable properties. In particular, they possess a high reactivity which makes them particularly interesting for the synthesis of long nucleotide sequences.

Thus, the object of the invention is to provide novel purine nucleoside derivatives which exploit the advantages of the modified adenine derivatives already developed by having available compounds possessing improved properties, in particular, enhanced reactivity.

The aim of the invention is also to furnish a process which allows these derivatives to be obtained in one step.

The aim of the invention is also the application of these derivatives to the preparation, in high yield, of oligonucleotide sequences which can be used in biology, especially as detection probes.

The derivatives of the invention which, as defined above, consist of adenine moieties capable of forming, after deprotection of the active functions, three hydrogen bonds with the reactive groups of the pyrimidine bases (thymine, uracil), are characterised in that the sugar component is substituted in position 3' or in position 5' by a phosphite or phosphoramidite group of formula I:

in which:

$R_1$ represents a lower alkyl radical, in particular a methyl radical or $-(CH_2)_n-CN$, n being an integer between 1 and 4;

X represents a halogen atom or a primary, secondary or tertiary amino group.

In one preferred group, X represents a halogen atom, in particular a chlorine atom or a bromine atom.

In another preferred group, X represents an amino group, especially a tertiary amino group. Groups particularly appropriate for use in the invention include the radicals dimethylamino, diethylamino, dipropylamino, diisopropylamino, morpholino, pyrrolidino and 2,2,6,6-tetramethylpiperidino.

In another preferred group, X represents a secondary amino group resulting from the elimination of a hydrogen atom from the ring of an unsaturated nitrogen heterocycle such as tetrazole, imidazole, substituted imidazoles of the nitroimidazole type, indole, pyrazole, benzimidazole, isoindole, pyrrole, triazole, dioxazole and analogues.

In an advantageous manner, the substitution of the sugar component linked to the modified adenines with a phosphoramidite group of the formula I confers on the corresponding products a high reactivity which enables long nucleotide sequences to be readily prepared and makes it possible to use them in the standard machines for oligo- and polynucleotide synthesis.

In addition, the NMR spectra demonstrate the high degree of purity of these products which makes them valuable for obtaining high coupling yields in the synthesis of oligonucleotides.

The adenine moieties of the derivatives of the invention are modified preferentially by the introduction at position C-2 of the pyrimidine ring of a group which, after deprotection, is capable of forming a hydrogen bond with the oxygen atom attached to the C-2 position of thymine or uracil.

According to a preferred embodiment of the invention, the nucleoside derivatives bear at the position C-2 of the pyrimidine ring of adenine, (a) an amino group, (b) a hydroxyl group $-OH$, or (c) a sulfhydryl group $-SH$, these groups being protected by the replacement of the hydrogen atom, or of the two hydrogen atoms in the case of the amino group, by a protecting group; of the kind usually used for these types of function.

In a preferred family of nucleosides, the derivatives have an amino group at the position C-2 and correspond to the formula II

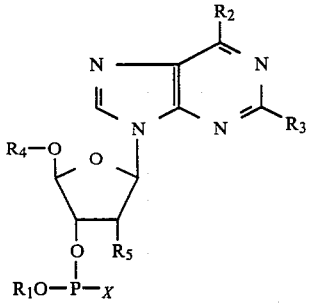

(II)

in which:
- $R_1$ and X are as defined above, X preferably representing the preferred meanings of the different groups considered,
- $R_2$ represents a group $—NH(A_1)$ or $—N(A_1,A_2)$,
- $R_3$ has the meanings of $R_2$ or represents a group $—O(A_1)$ or $—S(A_1)$.
- $A_1$ and $A_2$, identical or different, being chosen from among acyl groups, in particular, acetyl and benzoyl, butyryl, isobutyryl and other similar groups capable of being removed without modification of the nucleoside component or of the nucleotide chain formed from these components,
- $R_4$ represents a protecting group for the —OH function in position 5', in particular, a group chosen from among the radicals trityl, methoxytrityl, dimethoxytrityl, dialkoxyphosphite, pivalyl, isobutyloxy carbonyl, t-butyldimethylsilyl, and
- $R_5$ represents a hydrogen atom or a group $—OR_6$ with $R_6$ having the meanings of $A_1$, $A_2$ or $R_4$.

In a preferred group of this family, $R_3$ represents an amino group protected by $A_1$ and, if necessary, by $A_2$.

In another preferred group, $R_3$ represents an —OH group, protected, if necessary, as indicated above.

In yet another preferred group, $R_3$ represents a group $—SA_1$.

In accordance with the invention, the nucleoside derivatives defined above are obtained by reaction, in the presence of an inert gas of (a) a derivative of adenosine of the formula (III), substituted by the desired reactive groups in protected form and bearing a free —OH at position 3' of the sugar component, with (b) a phosphite of formula (IV). The reaction scheme which leads to protected nucleosides of formula (V) may be presented as follows:

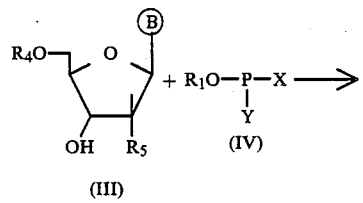

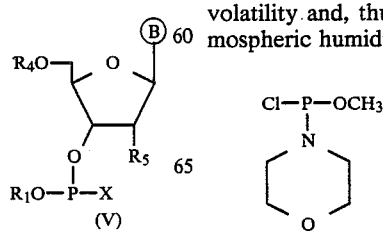

In these formulae X and $R_1$ are as defined above, Y represents a reactive grouping capable of reacting with the free —OH group of the sugar component, leading to the establishment of a bond between O and P and giving rise to a readily removable compound YH, and B represents a modified adenine moiety.

The above reaction principle can be applied to the synthesis of nucleosides containing a phosphoramidite group in position 5' by the use of a nucleoside of formula III above in which the —OH group at 5' is free and the —OH group at 3' is protected, for example, by a substituent of the type $R_4$.

In the preferred derivatives, account being taken of their high reactivity and the ease of their preparation, Y represents a halogen atom, more especially, a chlorine atom.

Preferably, X represents a group —N,N-diisopropyl; $—N[CH(CH_3)_2]$, —N—morpholino:

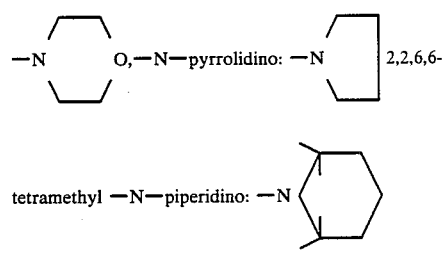

and $R_1$ represents an alkyl radical, more particularly a methyl radical or $—(CH_2)_n—CN$, n being an integer between 1 and 4, preferably 2.

In order to prepare the derivatives in which the base B bears an $—NH_2$ group at the position C-2, it is particularly preferable to utilise O-dimethoxytrityl-5'N,N-diisobutyryl amino-2 desoxy-2'adenosine, prepared from desoxy-2' guanosine, by analogy with the technique applied to thymidine and described by W. L. Sung in J. Chem. Soc. (Communication, 1089 (1981)).

The preparation of the derivatives in which the base B is modified at the position C-2 of the pyrimidine by an —OH group is carried out in a satisfactory manner from O-dimethoxytrityl-5' N-isobutyryl hydroxy-2-desoxy-2' adenosine which may also be prepared from the corresponding guanosine nucleoside derivative by analogy with the method of J. DAVOLL in J.A.C.S. 1951, 73 p. 3174—and in Nucleic Acid Chemistry ed. L. D. Townsend R. S.—Tipson in part. 2 page 565 John Wiley N.Y. 1978

In the case of derivatives containing a base B modified at the position C-2 by an —SH group, it is preferable to use O-dimethoxytrityl-5' N-isobutyryl mercapto-2 desoxy-2' adenosine which may be prepared in a manner similar to that for the corresponding 2-hydroxy derivative, by replacing the —OH group by an —SH group according to known methods.

The phosphorochloridites preferred for their reduced volatility and, thus, for their lower reactivity with atmospheric humidity include the following derivatives:

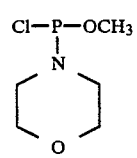

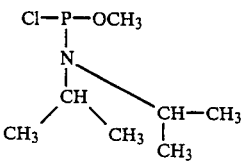

In accordance with a preferred step of the invention, an excess of the phosphite is used: this excess is preferably higher than twofold and more particularly of the order of threefold.

The reaction between the compounds III and IV is carried out preferably in the presence of a base, in particular an organic amine.

According to another procedure, the reaction is carried out at room temperature until the adenosine derivative starting material has disappeared, which is easily verified by thin layer chromatography, for example.

In order to facilitate the reaction, the protected adenosine derivative is dissolved in an organic solvent such as dichloromethane, tetrahydrofuran, acetonitrile or dioxane.

It is an advantage to purify the product obtained.

The purification process may include one or several steps of washing, drying, filtration, evaporation to dryness followed by the product being taken up again in the kind of organic solvent such as toluene, precipitation by means of a kind of organic solvent such as petroleum ether, centrifugation, drying of the precipitate and column chromatography of the precipitate recovered after centrifugation.

The nucleosides obtained represent particularly interesting synthetic intermediates, owing particularly to their high reactivity. They give coupling yields of higher than 95% in the assembly of nucleotide sequences and are just as readily usable in manual as in automated synthesis of these sequences.

These oligonucleotide sequences containing or built up from these nucleosides are able to hybridise advantageously with a complementary nucleotide sequence with great stability and high sensitivity and thus represent probes of great interest for the detection and analysis of nucleotide sequences of a given composition, particularly in the field of microbiological diagnostics, genetic errors or any other field in which hybridisation between nucleic acids is implicated.

They are particularly appropriate for replacing mixed probes in the detection and isolation of nucleotide sequences, for example, of messenger RNAs (m-RNA) or complementary DNAs (c-DNA).

In a manner particularly to be preferred this probe gives, in fact, a hybridisation analogous to that of a mixed probe and confers an analogous sensitivity for detection after hybridisation with complementary sequences when it represents a sequence deduced from a particular sequence of amino acids in which each degeneracy is substituted by one of the nucleotides of the degeneracy, in particular, T in the case of the degeneracy C/T and G in the case of the degeneracy G/A, and at least a part of the adenine moieties is replaced by modified adenine moieties such as those defined above.

These probes constituted of a sequence deduced from a particular amino acid sequence and in which each degeneracy is substituted by one of the nucleotides of the degeneracy, in particular T in the case of the degeneracy C/T and G in the case of the degeneracy G/A are described in the patent application FR No. 84 13095 referred to above.

In order to obtain a higher sensitivity of detection it is preferable to substitute adenine moieties as defined above for all the adenine moieties of the nucleotide fragment.

For most of the applications, the probe according to the the invention contains twenty nucleotides, but a longer fragment may be used for special applications.

The principal step in the preparation of these probes consists in the condensation of the —OH group at the 5' position of the sugar component of one nucleoside (1), covalently attached to a solid support, more particularly, a polymeric support such as silica gel or glass beads or polyacrylamide, with (2), a phosphoramidite derivative of adenosine, according to the following scheme:

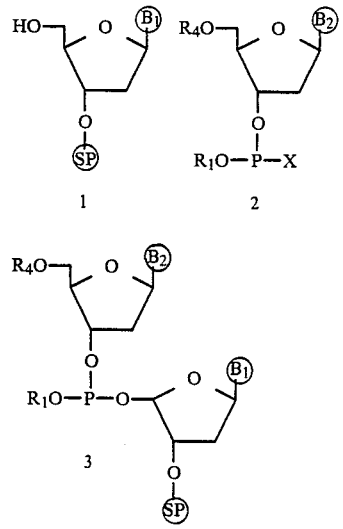

This reaction is preferably catalysed by 1H-tetrazole in acetonitrile.

After oxidation and removal of the protecting group at position 5' of the sugar component, the condensation operation is repated until the oligonucleotide of the desired length has been obtained and, if necessary, the solid support is removed.

It will be noted that the oligonucleotide sequences of these probes may contain, in accordance with the application FR No. 84 13 096 of Aug. 22, 1984, in the name of the applicants, in addition to the above derivatives and the bases usually used in the synthesis of oligonucleotides other bases, the presence of which may be deemed necessary, in particular, the modified bases X and/or Y. It is to be recalled that these modified bases give a mixture on deprotection, in particular, an equimolecular mixture, according to the reaction conditions, of uracil and cytosine or of thymine and methyl-5-cytosine, on the one hand, and of guanine and amino-2 adenosine on the other, according to the scheme:

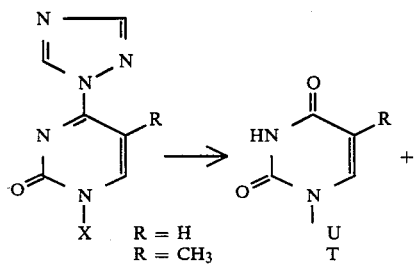

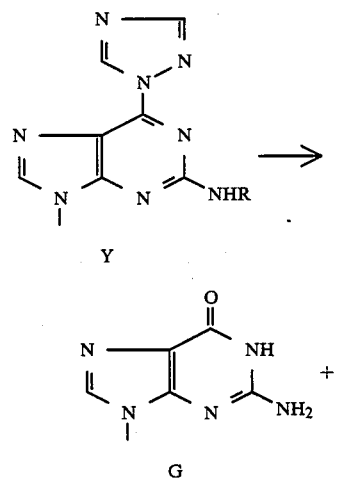

For their application in the field of biological analyses and extractions the probes are labelled according to the standard techniques with a view th their location after hybridisation.

These probes are readily accessible to various reagents, in particular, to specific antibodies to the bases, especially monoclonal antibodies.

The probes, prepared from the derivatives of the invention, may be used preferentially in techniques of analysis or extraction, particularly of messenger RNAs or complementary DNAs, implicating methods of detection involving the formation of immune complexes, in particular, immuno-enzymatic reactions.

By means of the phosphoramidite derivatives of the invention, appropriate nucleotide fragments have been prepared to isolate the c-DNA of antithrombin III, as described in the patent application FR No. 84 13095.

The study of the probes synthesised by means of phosphoramidites shows that they function like the probes prepared from the phosphotriesters of the patent application FR above.

Owing to the high reactivity of the phosphoramidites synthesised, the invention furnishes the means to exploit the advantages of the modified adenines used in the probes already prepared by the applicants, in particular, those of higher stability of the hybrids formed, higher sensitivity of detection after hybridisation of the nucleotide sequence to be analysed and the possibility of their being used in conjunction with methods of identification utilising immunologic (immuno-enzymatic) reactions instead of detection by radioactivity used hitherto.

In the examples which follow other characteristics and and advantages of the invention are reported.

EXAMPLE 1 dimethoxy trityl-5' $N_2N_6$ diisobutyrylamino-2-adenosine diisopropyl amino methoxy phosphine-3' of the formula:

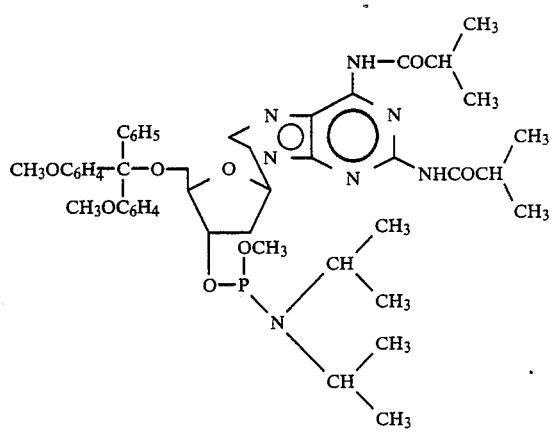

In a 5 ml, oven-dried flask are placed 200 mg (0.282 mmole) of dimethoxytrityl-5' desoxy-2' amino-2$N_2N_6$ diisobutyryl adenosine dissolved in 0.912 ml of dichloromethane distilled from $Na_2CO_3$ and 0.384 ml of redistilled diisopropylethylamine. After displacement of the air with helium the flask is closed with a septum. Then is added rapidly with a syringe 180.1 mg (0.912 mmole) which corresponds to 3.2 fold excess of diisopropylamino chloromethoxy phosphine. The mixture is stirred for 10 mn at room temperature and checked by TLC ($CH_2Cl_2$ 7.5% MeOH v:v) for absence of starting material. The reaction mixture is diluted with dichloromethane washed beforehand with saturated $NaHCO_3$. The mixture was washed quickly with saturated $NaHCO_3$, dried over sodium sulfate, filtered and evaporated to dryness. The residue is taken up in ca. 3 ml of redistilled toluene and precipitated with ca. 60 ml of redistilled petroleum ether cooled to $-70°$ C. (alcohol-Dry ice). As the precipitate remains in suspension, centrifugation is carried out for 5 mn at 5,000 rpm. The supernatant is decanted and the precipitate is well dried under vacuum. Subsequently, the product is rapidly chromatographed on a column of silica 9385 Merck (2.5 g), prepared with a mixture of dichloromethane/2% redistilled triethylamine for slight deactivation. Elution with pure dichloromethane. The product is eluted rapidly. After evaporation in dryness, the product is precipitated with petroleum ether. After evaporation of the supernatant to dryness, a white powder is obtained:

230 mg. Yield: 93%

Rf: ($CH_2Cl_2$ 7.5% MeOH): 0.72; Rf: start.mat.: 0.5 (AcOET 25% EP): 0.54; Rf: start.mat.: 0

MS (EI): 290 B+2; 303 DMT (CI, $NH_3$) 870 M+1, 218 $A^{iBu}$, 41 V DMT desoxyribose, 580 DMT desoxyribose phosphoramidite NMR ($CDCl_3$, $H_3PO_4$ internal reference: $-149.6$ ppm sextuplet, J 12.2 Hz.

EXAMPLE 2

Isolation of DNA complementary to antithrombin III

The amino acid sequence taken into consideration is the following:

²⁵¹Met Met Tyr Gln Glu Gly²⁵⁶ which corresponds to the m-RNA sequence:

5' AUG AUG UA$_U^C$CA$_G^A$GA$_G^A$G—3' and a c-DNA may be written:

5' ATG ATG TA$_C^T$CA$_G^A$GA$_G^A$G 3' and which contains three ambiguities.

In order to study the hybridisation with this c-DNA the following probes were prepared, namely:
as control, a mixed probe No. 1

3' T$\overset{*}{A}$C T$\overset{*}{A}$C AT$\overset{*}{_G^A}$GT$_T^C$CT$_T^C$ C 5' a sequence according to the invention containing modified adenine moieties:

3' TAC TAC AT<u>G</u> GTT T<u>T</u> C 5'

In these sequences A represents the moiety 2-amino 2'-deoxy adenosine. The moieties underlined—correspond to the site of degeneracy chosen (in the case of a degeneracy C/T, T is chosen and in the case of a degeneracy G/A, G is chosen). Those underligned correspond to a mismatch. The syntheses of these probes are carried out as follows:

(a) synthesis of the mixed probe No. 1.

The mixed probe was synthesised from 19 mg of resin T (resin bearing the nucleotide T and prepared according to the technique of K. Itakura et al. described in Nucleic Acids Research (1980), 8; 5473) with the subsequent trimers prepared according to the technique of K. Itakura et al. indicated above.

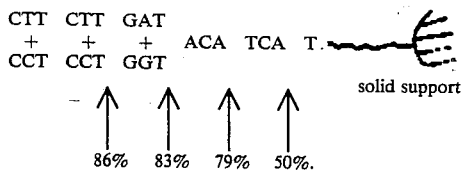

```
CTT    CTT    GAT
 +      +      +    ACA   TCA   T
CCT    CCT    GGT
       ↑      ↑      ↑     ↑          solid support
      86%   83%    79%   50%.
```

After the last coupling the resin is treated with 500 μl of a molar mixture of pyridine aldoxime (PAO) in tetramethyl guanidine (TMG), with 500 μl of TMG added overnight. After evaporation to dryness and heating with concentrated ammonia at 50° C. for 3 hours, the reaction mixture is purified by chromatography on a column of Sephadex G-10 (the company Pharmacia's commercial name for a column of cross-linked polysaccharide), followed by high pressure liquid chromatography (HPLC) on a reverse phase column. Subsequently, the mixture of oligonucleotides is detritylated with 80% acetic acid for 5 mn, evaporated to dryness (0 O.D.) (1 O.D.=one optical density unit, corresponding to 20-40 μg of sequence) and purified by preparative electrophoresis on acrylamide gel.

(b) synthesis of the sequence No. 2 according to the invention (with A)

The sequence containing A is synthesised from 30 mg of resin T

CTT CTT GGT $\overset{*}{A}$ C $\overset{*}{A}$ TC $\overset{*}{A}$ T

These probes are labelled with ³²P as follows: 50 μCi of [γ—³²P] ATP are added to 100 pmoles of the probe in a volume of 4 μl of mix and 0.5 μl of polynucleotide kinase (activity: 5–20×10³ units/ml, Boehringer Mannheim). The mixture is left at 37° C. for half an hour (T. Maniatis et al. Molecular Cloning, Cold Spring Harbor Lab. (1982)). The reaction is stopped by addition of 1.3 μl of buffered bromophenol blue, 100 mM of EDTA, 50% glycerol. The labelled product is purified on a gel (0.4×30×40 cm) containing 19 g of bisacrylamide, 19 g of acrylamide and 10 ml of 1M tris borate in a total volume of 100 ml.

The electrophoresis, programmed at 2,000 V, 43 W, 40 mA, is stopped when the bromophenol blue marker has migrated one third of the length of the plate. The radioactive band is cut out and extracted overnight in 2 ml of water. Hybridisation is carried out as follows:

2 colonies containing a complete c-DNA for $AT_{III}$ and 2 colonies containing a c-DNA unrelated to $AT_{III}$ are each inoculated on to 3 plates of complete medium containing 50 μg/ml of ampicillin. The colonies are transferred to 3 filters of Whatman 541, amplified for 20 hours on plates containing 250 μg/ml of chloramphenicol and prepared for hybridisation according to the technique described by J. P. Gergen et al. in Nucleic Acids Research (1979), 7, 2115. The filters were prehybridised for 2 hours at 42° C. in 6 NET (1 NET=0.15M NaCl, 0.0.15M tris HCl pH=7.5, 0.001M EDTA). 0.5% Monidet P40 (commercial name for a detergent), 100 μg/ml of yeast tRNA and 100 μg/ml of sonicated salmon sperm DNA (technique of T. Maniatris et al. in the article cited above). Hybridisation was carried out at 42° C. for 20 hours in the same solution in the presence of 10⁶ cpm of oligonucleotide labelled at 5' with [γ—³²P] ATP, each filter being hybridised with one of the 2 probes. The filters were washed 4 times for 15 minutes at 40° C. in 6 SSC (1 SSC=0.15M NaCl, 0.015M sodium citrate, pH=7.2, 0.1% of sodium dodecyl sulfate (SDS)). The filters were subjected to autoradiography.

It is verified that hybridisation is visible with the mixed probe 1 (1 sequence in 8 is complementary to c-DNA) and with the specific sequence 2 bearing 3 $\overset{*}{A}$ (1 "mismatch" and 9/16 GC pairs).

We claim:

1. Adenosines having the formula:

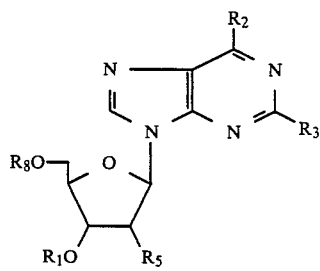

in which one of —OR₇ and —OR₈ is a phosphite or a phosphoramidite group of the formula

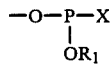

and the other of —OR$_7$ and —OR$_8$ or —OR$_4$, and wherein:

R$_1$ is a lower alkyl radical or —(CH$_2$)$_n$—CN, n being an integer of from 1 to 4;

X is a halogen atom, an amino group, or a member selected from the group consisting of tetrazolyl, imidazolyl, nitroimidazolyl, indolyl, pyrazolyl, benzimidazolyl, isoindolyl, pyrrolyl, triazolyl, dioxazolyl, dialkylamino, morpholino, pyrrolidino and piperidino groups;

R$_4$ is a hydroxyl protecting group;

R$_2$ is —NH(A$_1$) or —N(A$_1$, A$_2$);

R$_3$ is —NH(A$_1$), —N(A$_1$, A$_2$), —O(A$_1$) or —S(A$_1$);

A$_1$ and A$_2$ are identical or different and are selected from the group consisting of hydrogen and acyl groups;

R$_5$ is a hydrogen atom or a group —OR$_6$, wherein R$_6$ is hydrogen, an acyl group or a hydroxyl protecting group.

2. Adenosines according to claim 1, wherein R$_1$ represents a methyl group.

3. Adenosines according to claim 1, wherein R$_1$ represents —(CH$_2$)$_2$—CN.

4. Adenosine according to claim 1, wherein X is a chlorine atom, a bromine atom, or a member selected from the group consisting of dimethylamino, diethylamino, dipropylamino, diisopropylamino, morpholino, pyrrolidino, 2,2,6,6-tetramethylpiperidino, tetrazolyl, imidazolyl, nitroimidazolyl, indolyl, pyrazolyl, benzimidazolyl, isoindolyl, pyrrolyl, triazolyl, and dioxazolyl groups.

5. Adenosines according to claim 1, wherein A$_1$ and A$_2$, which are identical or different, are acyl groups selected from the group consisting of acetyl, benzoyl, butyryl and isobutyryl.

6. Adenosines according to claim 1, wherein R$_4$ is a protecting group selected from the group consisting of the radicals trityl, methoxytrityl, dimethoxytrityl, dialkoxylphosphite, pivalyl, isobutyloxy carbonyl and t-butyl-dimethylsilyl.

* * * * *